United States Patent [19]

Vaillancourt

[11] Patent Number: 5,122,123

[45] Date of Patent: Jun. 16, 1992

[54] CLOSED SYSTEM CONNECTOR ASSEMBLY

[76] Inventor: Vincent L. Vaillancourt, 14 Bunyan Dr., Livingston, N.J. 07039

[21] Appl. No.: 647,782

[22] Filed: Jan. 30, 1991

[51] Int. Cl.⁵ .............................. A61M 5/32
[52] U.S. Cl. ................... 604/192; 604/905; 604/283; 604/86
[58] Field of Search ............. 604/283, 284, 86, 88, 604/89, 905, 411, 414, 415, 192

[56] References Cited

U.S. PATENT DOCUMENTS 4,935,010 6/1990 Cox et al. ............... 604/905 X

FOREIGN PATENT DOCUMENTS 0256640 2/1988 European Pat. Off. ............ 604/905

*Primary Examiner*—John D. Yasko
*Attorney, Agent, or Firm*—Francis C. Hand

[57] ABSTRACT

The closed system connector assembly is formed with a male connector and a female connector. Both connectors have rubber membranes which can be pierced by a hollow needle disposed within the female connector. In some embodiments, the membrane of the female connector is mounted on a collapsible tube disposed about the hollow needle. During insertion of the male connector, this tube collapses and, upon withdrawal, the tube expands. In another embodiment, the female connector has a housing which carries the needle and is slidable within a sleeve which carries the membrane.

26 Claims, 3 Drawing Sheets

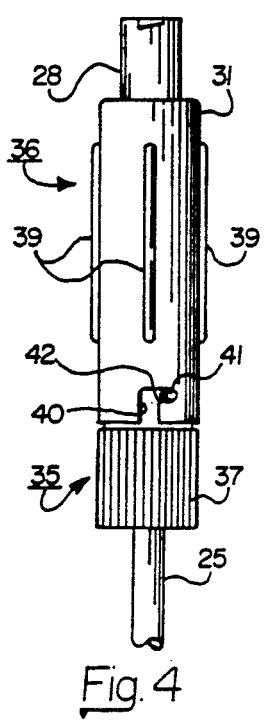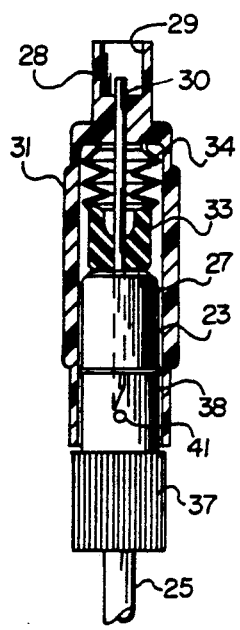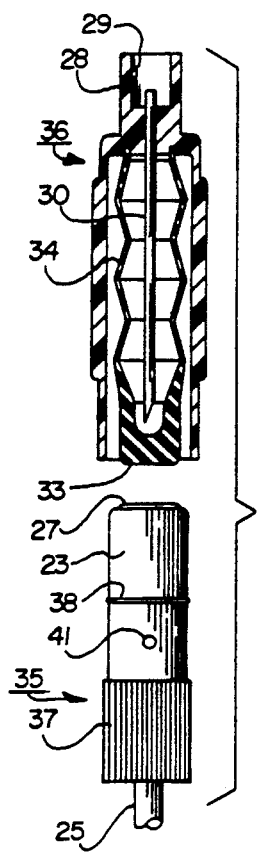
Fig. 4  Fig. 5  Fig. 3
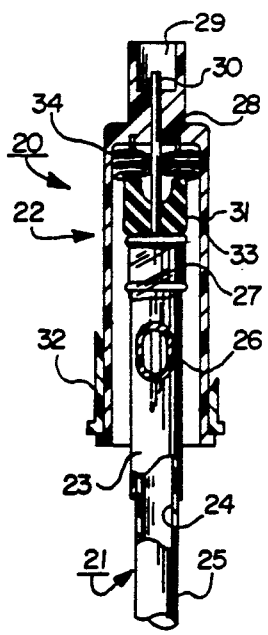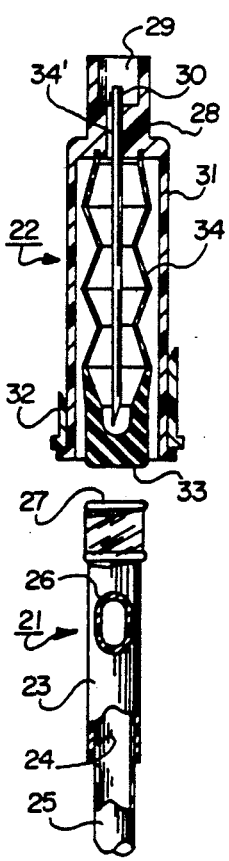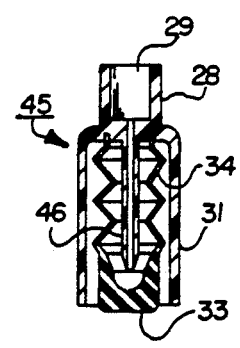
Fig. 8
Fig. 1  Fig. 2
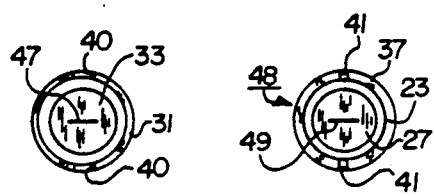
Fig. 9  Fig. 10

CLOSED SYSTEM CONNECTOR ASSEMBLY

This invention relates to a closed system connector assembly. More particularly, this invention relates to a a closed system connector assembly for use in the health care industry.

As is known, the health care industry is concerned with microorganisms such as bacteria and the like which may cause health problems. In some cases, people become patients because these microorganisms become unmanageable and threaten or endanger the health of the patient.

Patients requiring therapy are often placed in a position where their normal defenses against microorganisms are compromised. As a result, the patients may develop nosicomial infections while being treated for another disease during therapy. As has been recognized, a major cause of nosicomial infections has been due to connection/disconnection of tubing lines, especially in the area of IV therapy. This is one reason why most IV Administration Sets (IV tubing with connectors) are discarded every forty eight hours.

In the development of connectors for tubing lines, primary concern has generally always been with having a connector which can readily be closed and sealed and just as readily be opened with a minimum of force. A so-called luer connection is the generally accepted standard for the health care industry. This connector is easy to open and close and requires little force while at the same time providing a positive seal. However, one disadvantage of this connector is that after fluid flows through a connection made by the connector, if the practitioner (physician, nurse) wishes to open the connection and then reconnect the connection, the chance of microorganism contamination is sufficiently large that most hospitals do not allow this practice except under abnormal circumstances.

In order to provide a system which can be connected for the transfer of medication, followed by a sterile disconnection, the use of a Y-site connector has been developed. In this case, the connection is in the form of a plastic fitting having one end covered with a rubber septum. In order to deliver fluid into the connector, a sterile needle pierces through the rubber septum in order to transfer fluid into the line to which the connector is connected. After fluid transfer is completed, the needle is removed and the rugger septum self-closes to maintain what is commonly referred to as a closed system and sterility of the line is maintained. Everything associated with the now removed needle is considered to be non-sterile since the exit port of the needle is exposed to the atmosphere and almost immediately becomes contaminated.

In efforts to provide a system in which the connectors may be opened and then closed while maintaining sterility in both sections of the connector, a number of systems have been proposed, such as described in U.S. Pat. Nos. 3,886,930 and 3,986,508. In the first case, a blood collecting assembly is provided with a cannula mounted at one end in a recessed manner in a holder which, in turn, at one end can be fitted over a container in the form of a transparent glass tube. The opposite end of the cannula is covered over by a removable sheath which is mounted removed when a venipuncture is to be made. In addition, the assembly has been provided with a valve of elastomeric material which surrounds the cannula and which has an end wall through which the sharp end of the cannula is to pass in order to pierce through a resealable elastomeric closure on the evacuated container. After a disconnection, the valve is to return to a relaxed position with the end wall of the valve resealing. The overall assembly is, however, not suitable as a connector for tubing.

U.S. Pat. No. 3,986,508 describes a connector for blood processing employing a tubular male body element with a septum at one end and a tubular female body having a hollow needle for piercing the septum on the male body. In addition, a female septum of C form is positioned within one end of the female body with the needle extending within the open portion of the septum while being spaced a slight distance from the interior wall of the septum. When a connection is made, the needle pierces both septa. However, upon a disconnection, the needle remains exposed since the female septum is moved over the needle.

Accordingly, it is an object of the invention to provide a connector assembly which is simple in construction and has a demonstrated ability to retain sterility.

It is another object of the invention to provide a connector assembly that will retain a closed system at upstream and downstream portions of the connector assembly at all times.

It is another object of the invention to provide a connector assembly which can be readily made sterile on site immediately prior to forming a connection.

Briefly, the invention provides a closed system connector assembly comprising a male connector and a female connector which can be readily connected and disconnected to and from each other.

The male connector is constructed with a tubular portion to define a lumen and a membrane or septum at one end of the tubular portion for sealing the lumen.

The female connector has a housing defining a lumen, a membrane for sealing the lumen and for abutting the membrane of the male connector and a hollow needle mounted in the housing in communication with the lumen thereof. The needle is also disposed in facing relation to the membrane of the female connector and is of a length to pierce through the membranes of the two connectors to communicate the lumen of the male connector with the lumen of the female connector.

In one embodiment, the female connector has a biasing means for maintaining the membrane thereof in spaced relation to the end of the hollow needle. During insertion of the male connector, this biasing means collapses so as to permit the hollow needle to pass through the septum of the female connector as well as the septum of the male connector. After withdrawal of the male connector, the biasing means expands to again seal over the needle.

In another embodiment, the female connector is provided with a means for moving the needle relative to the membrane of the female connector in order to pierce through the two membranes and to communicate the two lumen to each other and, thereafter, to withdraw the needle from the two connectors.

The female connector may be provided with a tubular portion coaxial of the hollow needle for receiving the tubular portion of the male connector. In this embodiment, the membrane of the female connector is mounted on a collapsible tube which is secured to and between the housing and the membrane. In this case, the collapsible tube serves to maintain the hollow needle in a sterile condition until ready for use.

The connector assembly is such that both membranes are positioned for easy access at the ends of the respective connectors. Thus, just prior to a hook-up in a hospital or in the field, the exposed surfaces of the two membranes can be wiped with an antiseptic, such as povidone iodine. This antiseptic has the ability to almost immediately render the two surfaces sterile and, for this reason, is often the antiseptic of choice in hospitals. Once wiped, the two connectors can be placed in abutting position and the male connector moved into the female connector to achieve a connection of the respective lumen to each other.

This assembly may also be provided with means for securing the two connectors together. For example, the tubular portion of the female connector may be provided with a L-shaped slot while the tubular portion of the male connector is provided with a pin for sliding in the slot. Thus, after the two connectors have been axially moved relative to each other, a slight turn ca be used to positoin the pin within a transverse part of the slot.

Alternatively, the means for securing the two connectors together may employ an external thread on the tubular portion of the male connector and a mating internal thread in the tubular portion of the female connector. In this case, a connection is made by screwing the male connector into the female connector.

Each membrane which is used on the respective connectors may be provided with a centrally disposed slit for passage of the hollow needle. Further, the hollow needle may be made of plastic. In this case, coring of the membrane can be eliminated. In this respect, it is to be noted that a metal hollow needle upon piercing through a solid rubber membrane causes a core of rubber to be removed from the membrane. After several such punctures, leakage paths would eventually arise through the membrane. The use of a centrally disposed slit reduces the risk of coring. In addition, the use of a plastic needle substantially reduces the risk of coring since the plastic needle would tend to seek out the slit in order to pass through the membrane. In addition, the use of the slit permits a relatively large connector to be used, for example, the slit may provide a sealing effect for a twelve to sixteen gauge needle.

In the embodiment where the female connector is provided with a means for moving the needle relative to the membrane, the female connector can be provided with a separate tubular sleeve which is slidably mounted on the housing thereof coaxially thereof of the needle. In this case, the tubular sleeve has the membrane secured at one end while the hollow needle is secured to the housing. In addition, a collapsible rubber sheath may be secured to the housing and disposed coaxially about the needle. This embodiment also includes means for securing the two connectors together, for example, a means in the form of a collar which is slidably mounted on the male connector and which has an internal screw thread for threaded engagement with an external screw thread on the tubular sleeve of the female connector. In use, after the two connectors have been connected together via the collar, the housing of the female connector is slid forwardly into the tubular sleeve of the female connector so as to cause the hollow needle to pierce not only the two membranes but also the rubber sleeve. When the two connectors are to be disconnected, the housing is first pulled partially from the tubular sleeve of the female connector in order to withdraw the hollow needle. At the same time, the rubber, sleeve retunrs to a sealing position about the hollow needle. Thereafter, the two connectors can be disconnected.

In still another embodiment, the female connector may be constructed for use in an IV line in a manner as described in copending patent application Ser. No. 07/395,762, filed Aug. 18, 1989. In this respect, the female connector has a housing with a cylindrical portion defining a flow path perpendicular to the hollow needle while the needle has a side opening in communication with the flow path. In addition, a collapsible means is provided to permit pushing of the hollow needle through a membrane sealing the female connector as well as a membrane sealing a tubular portion of a male connector. This embodiment may also utilize suitable means for securing the two connectors together.

These and other objects and advantages of the invention will become more apparent from the following detailed description taken in conjunction with the accompanying drawings wherein:

FIG. 1 illustrates in partial cross section a connection made by the connector assembly constructed in accordance with the invention;

FIG. 2 illustrates an exploded view of the connectors for forming the connection of FIG. 1 in accordance with the invention;

FIG. 3 illustrates an exploded view of a modified connector assembly in accordance with the invention;

FIG. 4 illustrates a side view of a connection made with the connectors of FIG. 3;

FIG. 5 illustrates a part cross sectional view of the connection of FIG. 4;

FIG. 8 illustrates a cross sectional view of a female connector employing a plastic needle in accordance with the invention;

FIG. 9 illustrates an end view of the female connector of FIG. 8;

FIG. 10 illustrates an end view of a male connector employing a slit membrane in accordance with the invention;

Figure 6:
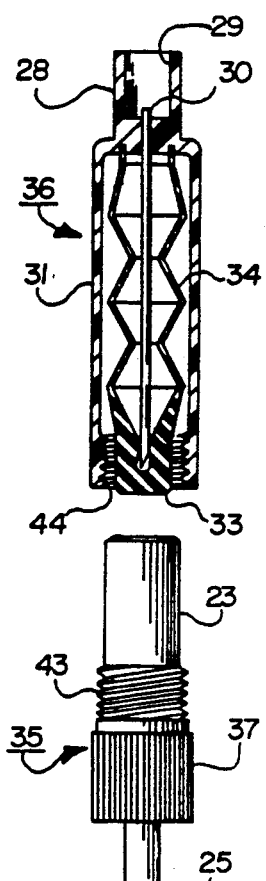
FIG. 6 illustrates an exploded view of a further modified connector constructed in accordance with the invention.

Referring to FIG. 1, the closed system connector assembly 20 has a pair of connectors 21, 22 which are connected together in a releasably fixed manner.

Referring to FIGS. 1 and 2, one connector 21 (male connector) is in the form of a Y-site connector having a tubular portion 23 defining a lumen 24 receiving a tube 25 as well as a branch arm 26 as is known. A membrane in the form of a rubber septum 27 is secured to the end of the tubular portion 23 for sealing the lumen 24, i.e. at the opposite end of the lumen 24 from the tubing 25.

The second connector 22 (female connector) has a housing 28, for example of transparent plastic, defining a second lumen 29 for receiving another connector or a tubing (not shown) and a hollow metal needle 30 which is mounted in the housing 28. In addition, the second connector 22 has a tubular portion 31 extending from the housing 28 coaxially of the needle 30 which is sized to receive the male connector 21 as shown in FIG. 1. A locking collar 32 is also rotatably mounted on the tubular portion 31 for securing the connector 21 in place. For example, the collar 32 is constructed in a manner as described in pending U.S. patent application Ser. No. 07/463,243, filed Jan. 10, 1990. To this end, the locking collar 32 has a slot for passage of the branch 26 of the Y-site connector 21 and a cam surface for moving under the branch 26 to obtain a fixed connection.

The female connector 22 also has a membrane in the form of a rubber septum 33 within the tubular portion 31 and a collapsible biasing means in the form of a collapsible tube 34 secured between the housing 28 and the membrane 33. As illustrated in FIG. 2, the collapsible tube 34 maintains the membrane 33 in spaced opposed relation to the end of the needle 30 while sealing the needle 30. As indicated in FIG. 1, the tube 34 is collapsible in order to permit the needle 30 to pierce through the membrane 33 as well as the membrane 27 of the Y-site connector 21 in order to communicate the lumen thereof with each other. The collapsible tube 34 is integral with the membrane 33 and is made, for example, of an elastomeric material. A secondary spring (metal) may be used in addition to the rubber collapsible tube 34 to give more springiness and instant closure.

In order to form a connection between the two connectors 21, 22, the exposed surfaces of the two membranes 27, 33 can be wiped with a suitable antiseptic. Next, the two membranes 27, 33 are brought into abutment and the Y-site connector 21 pushed into the tubular portion 31 of the female connector 22 to an extent as indicated in FIG. 1 wherein the hollow needle 30 has pierced through the two membranes 33, 27 so as to communicate the lumen 24, 29 together. When the two connectors 21, 22 are disconnected from each, the connectors take up the position as shown in FIG. 2, that is, the collapsible tube 34 expands to the unrestrained position so that the membrane 33 is disposed in spaced relation to the end of the hollow needle 30. In this respect, the membrane 33 is able to slide along the length of the needle 30 with the inherent resiliency or spring force of the tube 34 overcoming any friction between the membrane 33 and the needle 30.

As indicated in FIG. 2, a vent passage 34 may be provided in the housing 28 parallel to the needle 30 so as to permit venting of the interior of the tube 34 during collapsing into the position shown in FIG. 1.

Should a new connection be required, the two membranes 27, 38 are again wiped with an antiseptic and reconnection made.

Referring to FIG. 4, wherein like reference characters indicate like parts as above, a closed system connector assembly may be constructed of a relatively simple male connector 35 and a female connector 36. As indicated in FIG. 3, the male connector 35 has a tubular portion 23 extending from a knurled gripping portion 37 while a rubber membrane 27 is fixedly mounted within the end of the tubular portion 23 in a suitable manner. In addition, an annular ring or rib 38 is disposed about the tubular portion 23 for purposes as described below.

The female connector 36 includes a tubular portion 31 which is sized to slidably receive the male connector 35 via the annular rib 38 as indicated in FIG. 5. In addition, the female connector 36 is provided with a series of circumferentially spaced ribs 39 on the outside of the tubular portion 31 for gripping purposes.

As indicated in FIG. 4, a suitable means is provided for securing the two connectors 35, 36 together. This means includes a pair of L-shaped slot 40 (only one of which is shown) in the tubular portion 31 of the female connector 36 and a pair of pins 41 on the tubular portion 23 of the male connector 35 (only one of which is shown) for sliding within the slot 40. When bringing the two connectors 35, 36 together, the pins 41 slide axially within the long leg of the respective slots 40. Thereafter, the two connectors 35, 36 are rotated relative to each other so as to bring the pins 41 within the short transverse leg of the respective slots 40. In this respect, a tab or nose 42 can be provided on the tubular portion 31 of the female connector 36 so as to provide for a snap-fit of each pin 41 within a slot 40.

Where the female connector 36 receives tubing, for example, from an IV line (not shown) in the lumen 29, a need may arise to prime (purge) the line and female connector 36 prior to assembly to the male connector 35. In such a case, a hollow tube (not shown) can be slid into the tubular portion 31 of the female connector 36 to push the membrane 33 inwardly to expose the hollow needle 30. After a few drops have been effused from the line and needle 30, the hollow tube can be removed with the membrane 33 springing back into protective sealing relation over the end of the needle 33. Thereafter, the female connector 36 can be connected to a male connector 35 as described above.

The exposure of the needle end to atmosphere in this regard prevents air binding. Alternatively, an air filter may be used within the connector 36 in order to let air breath out while keeping fluid in.

It is to be noted that the hollow tube used to expose the needle for purging may include a pin 41 on the outside surface so that the hollow tube can be locked in place in a manner similar to a male connector 35. This would permit freeing of one's hand for other manipulative procedures.

Figure 7:
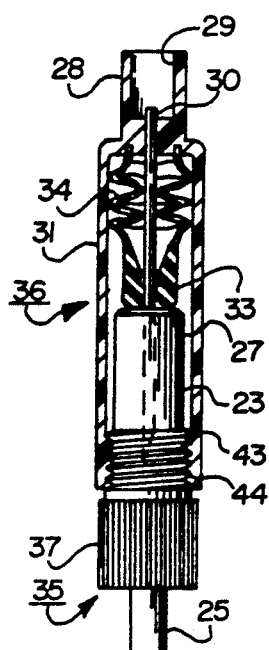
FIG. 7 illustrates a part cross sectional view of a connection made with the connectors of FIG. 6.

Referring to FIGS. 6 and 7, wherein like reference characters indicate like parts as above, the two connectors 35, 36 may be secured together by means of an external thread 43 on the tubular portion 23 of the male connector 35 and an internal mating thread 44 in the tubular portion 31 on the female connector 36.

Referring to FIGS. 8 and 9, wherein like reference characters indicate like parts as above, a female connector 45 may have a hollow plastic needle 46 integrally formed with the plastic housing 28. In addition, the membrane 33 may be provided with a centrally disposed slit 47 (see FIG. 9). In this case, the hollow plastic needle 46 need not have a sharp beveled end as the metal needle shown in FIG. 2. During collapsing of the elastomeric tube 44, the plastic needle 46 tends to seek out the slit 47 in the membrane 33 and, thus, avoid a coring situation in the membrane 33.

Of note, the slit 47 allows the use of a plastic conical shaped needle having a tip which is removed. This type of needle has very poor point sharpness properties and usually will not be able to pierce a rubber septum. However, the slit 47 allows such a plastic needle to actually pass through the rubber at the slit 47. Thus, when larger openings are desired through a rubber septum, the use of the slit not only allows for the use of a plastic needle but also gives the desired aperture.

Referring to FIG. 10, the membrane 27 provided on a male connector 48 also has a slit 39 to facilitate passage and sealing of the hollow needle 46 of the female connector 45 of FIG. 8.

Referring to FIGS. 11 to 14, wherein like references indicate like parts as above, the closed system connector assembly may be constructed in an alternative embodiment wherein a hollow needle 30 of a female connector 50 is movable relative to a sealing membrane 33.

Figure 11:
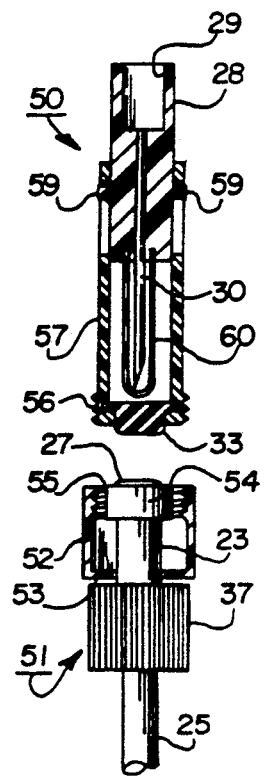
FIG. 11 illustrates an exploded view of a further modified connector assembly in accordance with the invention.

Referring to FIG. 11 the male connector 51 has a tubular portion 23 which slidably receives a collar 52. As indicated, the collar 52 has an inwardly turned flange 53 at a lower end which is received in a recess formed by the knurled portion 37 and a raised portion 54 on the tubular portion 23. In addition, the collar 52 has an internal screwed thread 55 for threaded engagement with an external screw thread 56 on the female connector 50 as indicated in FIG. 12.

Figure 15:
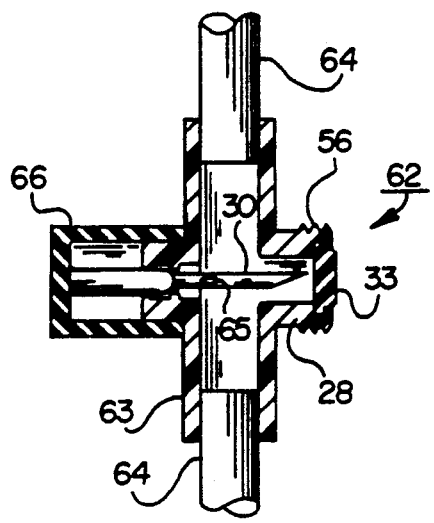
FIG. 15 illustrates a modified female connector constructed in accordance with the invention.

The female connector 50 includes a tubular sleeve 57 which is slidably mounted relative to the housing 28 and which carries the rubber membrane 33 at one end in sealing relation. A suitable means is also provided for securing the sleeve 57 to the housing 28. In this respect, as indicated in FIG. 15, the sleeve 57 has an L-shaped slot 58 while the housing has a pin 59 which is slidably received within the slot 58. As indicated in FIG. 12, pins mays be provided on diametrically opposite sides of the housing 28 for securement in respective slots 58 in the sleeve 57.

Referring to FIG. 11, the female connector 50 also has a collapsible rubber sheath 60 secured to the housing 28 at one end and disposed coaxially about the needle 30 in sealed relation.

Figure 12:
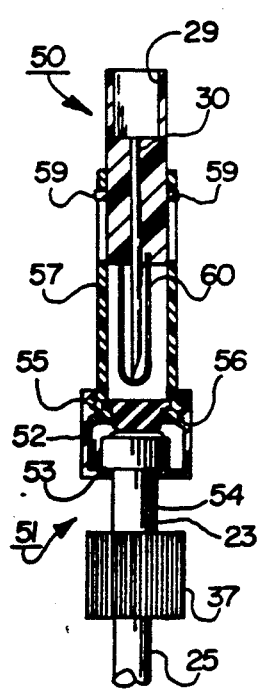
FIG. 12 illustrates a part cross sectional view of the connectors of FIG. 11 in an initially connected position.
Figure 13:
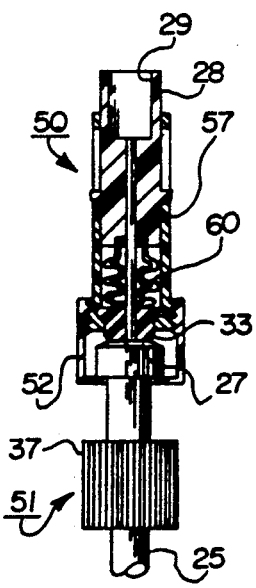
FIG. 13 illustrates a part cross sectional view of the connectors of FIG. 11 in a connected position.
Figure 14:
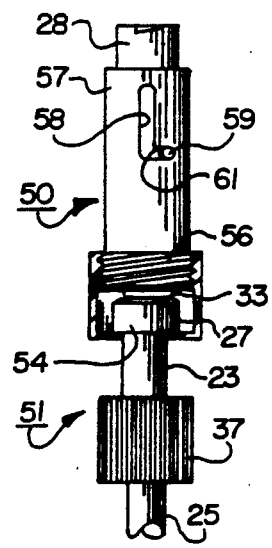
FIG. 14 illustrates a side view of the connection formed by the connectors of FIG. 11.

As indicated in FIG. 12, in order to form a connection between the two connectors 50, 51, the two membranes 27, 33 are sterilized, for example in a manner as described above. Thereafter, the two connectors 50, 51 are brought into coaxial alignment and the collar 52 on the male connector 51 is threaded onto the external thread 56 on the sleeve 57 of the female connector 50 until a snug fit is obtained. Next, the housing 28 of the female connector 50 is slid into the sleeve 57 so as to force the needle 30 through the rubber sleeve 60 and both membranes 33, 27 into a position as illustrated in FIG. 13. Thereafter, the housing 28 is rotated, for example to the right as viewed in FIG. 14, so as to move the pin 59 into the short transverse leg of the slot 58 to effect locking of the housing 28 relative to the sleeve 57. As indicated in FIG. 14, the suitable nose or the like 61 may be provided on the sleeve 57 to provide for locking of the pin 59 in place.

In order to disconnect the connection, a reverse sequence of steps is followed. During this time, the rubber sleeve 60 expands from the collapsed position shown in FIG. 13 into the expanded position shown in FIG. 12.

The use of the rubber sleeve 60 serves to improve the sealing arrangement of the needle 30 should a sufficient seal not be retained between the housing 28 and the sleeve 57.

Figure 16:
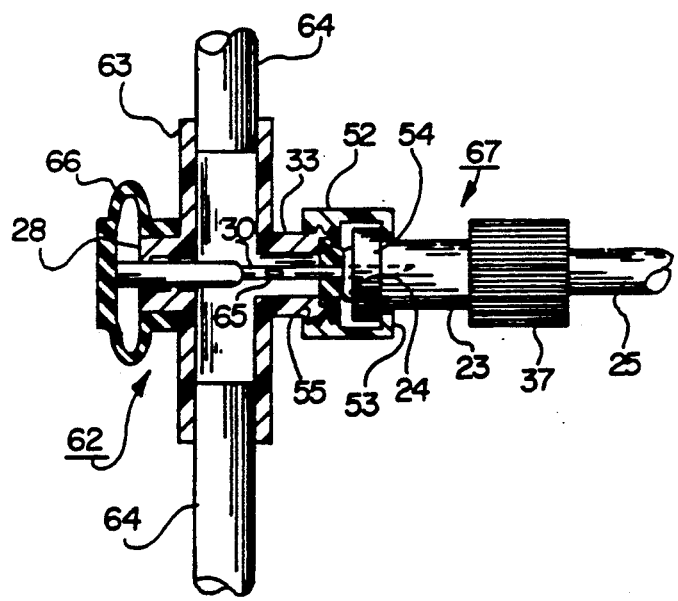
FIG. 16 illustrates a connection made with the female connector of FIG. 15 in accordance with the invention.

Referring to FIGS. 15 and 16, wherein like reference characters indicate like parts as above, the female connector 62 may be constructed with a housing 28 having a cylindrical portion 63 defining a flow path perpendicular to a hollow needle 30 mounted within the housing 28. As indicated, the cylindrical portion 63 forms a lumen to receive two tubes 64 of an IV line at opposite ends. In addition, the rubber membrane 33 is mounted on the housing 28 in spaced relation to the sharp end of the needle 30.

The needle 30 is also provided with an opening 65 in the side so as to communicate with the flow path formed by the cylindrical portion 63. Also, the needle 30 is slidably mounted within the housing 28 and cooperates with a collapsible means 66 which is disposed on the housing 28 for movement between an extended position, as shown in FIG. 15, with the needle 30 spaced from the membrane 33 and a collapsed position, as shown in FIG. 16, with the needle 30 piercing the membrane 33 as well as the membrane 27 of a male connector 67 constructed in a manner as illustrated in FIG. 11.

The collapsible means 66 is constructed in a manner similar to that as described in copending application Ser. No. 07/395,762, filed Aug. 18, 1989.

In use, in order to make a connection, the male connector 67 is brought into abutment with the female connector 62 and the collar 52 on the male connector 66 is threaded onto the external thread 56 of the female connector 62. Thereafter, the collapsible means 66 can be collapsed as indicated in FIG. 16 to have the needle 30 pierced through the two membranes 33, 27 to communicate the tubing 25 with the tubes 64.

The invention thus provides a closed system connector assembly of relatively simple construction which provides for a sterile connection and a sterile disconnection for a hollow needle.

The invention also provides a connector assembly in which there is a minimum potential for membrane coring, a minimum resistance to needle penetration and minimal generation of debris in piercing a membrane.

The invention also provides a connector assembly which hides a needle thereby providing a physiological effect of eliminating concerns that nurses may have of self-inflicted needle sticks.

Although IV therapy uses are referred to in disclosing this invention, the connector assembly also has significant appeal in many other areas of health care.

For example, in general nutrition, it has long been the object of many research endeavors to provide a sterile closed system for the delivery of nutrients. To date, providing pre-sterilized filled nutrient bags is the current state of the art. It is recognized that this delivery system is readily compromised and unless the product is delivered in a short space of time, there is little to be gained over conventional filling of the enteral bag at the bed site by a practitioner. The use of the above-described connector assembly in an enteral feeding set would now provide a closed system for the use with prefilled sterile nutrient bags for long term feeding.

Ambulatory peritoneal dialysis requires a sterile connection to enable the user to connect/disconnect bags of dialysis solutions. The sterile system currently recognized as being workable includes the use of UV light. Unfortunately, this system, from the viewpoint of the patient management, has many disadvantages. UV light must be controlled otherwise the patient can suffer damage as a result of exposure. As a result, the system does not enjoy the widespread usage that an accepted up and down stream closed system would be expected to have. The connector assembly described above provides a simple, easy to manipulate, inexpensive and most importantly an accepted sterile closed system transfer.

Arterial lines are noted for being susceptible to contamination. Stopcocks particularly are recognized as sites for microorganism growth. The use of the connector assembly described above would not only alleviate this concern but allow physicians to open and close the main line without fear of contamination. Presently, main lines as a general practice may not be open and reconnected.

What is claimed is:

1. A closed system connector assembly comprising
a first connector having a tubular portion defining a first lumen for a fluid and a first membrane at one end of said tubular portion sealing said lumen; and
a second connector having a housing defining a second lumen for a fluid, a second membrane for coaxially abutting said first membrane, a hollow needle mounted in said housing in facing relation to said second membrane and having an opening in communication with said second lumen and collapsible means maintaining said needle and said second membrane in opposed spaced relation and being collapsible to permit said needle to pierce through said second membrane and said first membrane to communicate said first lumen and said second lumen with each other.

2. A closed system connector assembly as set forth in claim 1 wherein said second connector has a tubular portion coaxial of said needle for receiving said first connector therein.

3. A closed system connector assembly as set forth in claim 2 wherein said collapsible means is a collapsible tube disposed between said housing and said second membrane coaxially of said needle.

4. A closed system connector assembly as set forth in claim 1 wherein said housing has a cylindrical portion defining a flow path perpendicular to said needle with said opening of said needle being in communication with said flow path.

5. A closed system connector assembly as set forth in claim 4 which further comprises means for securing said connectors together with said membranes in abutting relation.

6. A closed system connector assembly comprising
a male connector having a tubular portion defining a first lumen for a fluid and a membrane at one end of said tubular portion sealing said lumen; and
a female connector having a housing defining a second lumen for a fluid, a tubular portion for receiving said one end of said male connector therein, a hollow needle mounted in said housing, a collapsible tube secured to said housing and extending coaxially of said needle and a second membrane secured to said tube in spaced relation to said needle for abutting said first membrane in response to insertion of said end of said male connector into said tubular portion of said female connector.

7. A closed system connector assembly as set forth in claim 6 which further comprises means for securing said connectors together.

8. A closed system connector assembly as set forth in claim 7 wherein said means includes an L-shaped slot in said tubular portion of said female connector and a pin on said tubular portion of said male connector for sliding in said slot.

9. A closed system connector assembly as set forth in claim 7 wherein said means includes an external thread on said tubular portion of said male connector and a mating internal thread in said tubular portion of said female connector.

10. A closed system connector assembly as set forth in claim 6 wherein each membrane has a centrally disposed slit for passage of said needle.

11. A closed system connector assembly as set forth in claim 10 wherein said needle is made of plastic.

12. A closed system connector assembly comprising
a male connector having a tubular portion defining a first lumen and a first membrane at one end of said tubular portion sealing said lumen; and
a female connector having a housing defining a second lumen, a second membrane for sealing said second lumen and for abutting said first membrane, a hollow needle mounted in said housing in communication with said second lumen, said needle facing said second membrane and being of a length to pierce through said second membrane and said first membrane to communicate said first lumen with said second lumen, and biasing means for maintaining said second membrane in spaced relation to said needle.

13. A closed system connector assembly as set forth in claim 12 wherein said biasing means is a collapsible tube secured to and between said housing and said second membrane of said female connector.

14. A closed system connector assembly as set forth in claim 12 wherein said female connector has a tubular portion coaxial of said needle for receiving said tubular portion of said male connector therein.

15. A closed system connector assembly as set forth in claim 12 wherein each membrane has a centrally disposed slit for passage of said needle.

16. A closed system connector assembly as set forth in claim 15 wherein said needle is made of plastic.

17. A closed system connector assembly comprising
a first connector having a tubular portion defining a first lumen for a fluid and a first membrane at one end of said tubular portion sealing said lumen; and
a second connector having a housing defining a second lumen for a fluid, a second membrane at one end for coaxially abutting said first membrane, a hollow needle mounted in said housing in facing relation to said second membrane and an opening in communication with said second lumen and means for moving said needle relative to said second membrane to pierce through said second membrane and said first membrane to communicate said first lumen and said second lumen with each other.

18. A closed system connector assembly as set forth in claim 17 wherein said means includes a tubular sleeve slidably mounted on said housing coaxially of said needle and having said second membrane secured at one end thereof.

19. A closed system connector assembly as set forth in claim 18 which further comprises a collapsible rubber sheath secured to said housing at one end and disposed coaxially about said needle.

20. A closed system connector assembly as set forth in claim 17 which further comprises means for securing said connectors together.

21. A closed system connector assembly as set forth in claim 20 wherein said means for securing said connectors together includes a collar slidably mounted on said male connector and having an internal screw thread, and an external screw thread on said female connector for mating with said internal screw thread.

22. A closed system connector assembly as set forth in claim 17 wherein each membrane has a centrally disposed slit for passage of said needle.

23. A closed system connector assembly as set forth in claim 22 wherein said needle is made of plastic.

24. A closed system connector assembly comprising a first connector having a tubular portion defining a first lumen for a fluid and a first membrane having an exposed surface at one end of said tubular portion sealing said lumen; and a second connector having a housing defining a second lumen for a fluid, a tubular portion extending from said housing for receiving said first connector therein, a second membrane having an exposed surface at one end of said tubular portion for coaxially abutting said first membrane, a hollow needle mounted in said housing in facing relation to said second membrane and having an opening in communication with said second lumen and collapsible biasing means maintaining said needle and said second membrane in opposed spaced relation and being collapsible in response to reception of said tubular portion of said first connector in said tubular portion of said second connector to permit said needle to pierce through said membrane and said first membrane to communicate said first lumen and said second lumen with each other.

25. A closed system connector assembly as set forth in claim 24 wherein said collapsible means is a collapsible tube disposed between said housing and said second membrane coaxially of said needle.

26. A closed system connector assembly as set forth in claim 24 wherein each membrane is a rubber septum.

* * * * *